United States Patent
Gaudl et al.

(10) Patent No.: US 6,348,594 B2
(45) Date of Patent: *Feb. 19, 2002

(54) PROPYLENE UREAS AND PROCESS FOR THEIR PREPARATION

(75) Inventors: Kai-Uwe Gaudl; Artur Lachowicz; Gerwald Grahe, all of Berlin (DE)

(73) Assignee: Dainippon Ink and Chemicals, Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/363,652

(22) Filed: Jul. 30, 1999

(30) Foreign Application Priority Data

Jul. 31, 1998 (DE) .......................... 198 34 684

(51) Int. Cl.⁷ ............................................. C07D 239/02
(52) U.S. Cl. ................................. 544/318; 525/328.8
(58) Field of Search ......................................... 544/318

(56) References Cited

U.S. PATENT DOCUMENTS

| 4,770,668 A | | 9/1988 | Skoultchi et al. | |
| 4,854,934 A | * | 8/1989 | Wilhelm et al. | ............ 544/318 |

* cited by examiner

*Primary Examiner*—D. R. Wilson
(74) *Attorney, Agent, or Firm*—Armstrong, Westerman & Hattori, LLP

(57) ABSTRACT

Urea derivatives of formula 1 for the hardening of hydroxyl group-containing polymers,

1

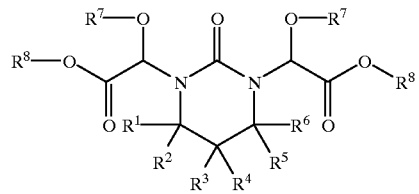

wherein each of $R^1$–$R^7$ is a hydrogen atom or a linear or branched $C_1$–$C_4$-alkyl group, preferably methyl, ethyl, n-propyl, isopropyl, n-butyl or isobutyl, $R^1$–$R^7$ being identical or different, and $R^8$ is a linear or branched $C_1$–$C_6$-alkyl group, preferably methyl, ethyl, n-propyl, isopropyl, n-butyl or isobutyl. The compounds 1 are prepared by reacting a compound 2

2

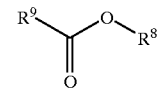

wherein $R^9$ is a member selected from the group consisting of —CHO, —CH(OH)—$OR^8$ and —CH(OH)$_2$ with a urea derivative 3

3

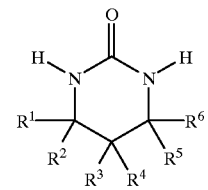

optionally followed by etherification of the reaction product with an alcohol X—OH, wherein X is a linear or branched $C_1$–$C_4$-alkyl group.

6 Claims, No Drawings

PROPYLENE UREAS AND PROCESS FOR THEIR PREPARATION

The invention relates to new urea derivatives of the formula 1,

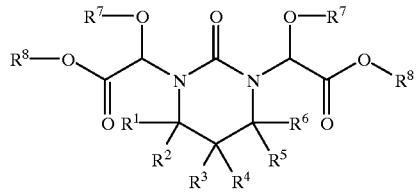

in which each of $R^1$–$R^7$ represents a hydrogen atom or a linear or branched $C_1$–$C_4$-alkyl group, in particular methyl, ethyl, n-propyl, isopropyl, n-butyl or isobutyl, wherein $R^1$–$R^7$ may be identical or different, and $R^8$ represents a linear or branched $C_1$–$C_6$-alkyl group, in particular methyl, ethyl, n-propyl, isopropyl, n-butyl or isobutyl. The invention also relates to a process for preparing compounds of the general formula 1. In addition, the invention relates to the use of compounds of the formula 1 for hardening hydroxyl group-containing polymers.

Reaction products of ethylene ureas and glyoxylic acid derivatives are known from U.S. Pat. No. 4,770,668. They are used to cross-link hydroxyl group-containing polymers, in particular for cross-linking hydroxyl groups within cellulose fibers. These cross-linking agents are prepared at temperatures of 100–140° C. In this temperature range oligomerization of these reactive cross-linking agents already takes place because they can also react with themselves, such as is the case, e.g., for urea/formaldehyde amino resins (R. Wegler in Houben-Weyl "Methoden der organischen Chemie", Volume 14/2 (1963), pages 320–328). Oligomerization causes a reduction in effectiveness as cross-linking agents, particularly when cross-linking cellulose fibers, since the oligomerized cross-linking agent can no longer penetrate sufficiently far into the cellulose fiber due to its increased weight and size.

Furthermore, the high temperatures of preparation also lead to some discoloration of the products (see Examples 4.2, 4.4 and 4.5 in U.S. Pat. No. 4 770 668), which is a disadvantage when they are used to coat or impregnate colorless materials.

The object of the invention is therefore to overcome the defects in the prior art mentioned above, in particular the production of oligomeric fractions and discoloration, and to provide improved cross-linking agents based on urea which are free of the disadvantages mentioned above.

This object is achieved by the invention. The invention provides compounds of the formula 1,

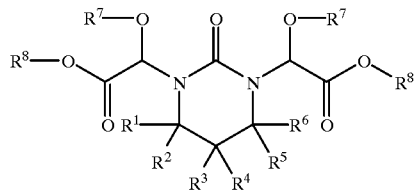

in which each of $R^1$–$R^7$ represents a hydrogen atom or a linear or branched $C_1$–$C_4$-alkyl group, in particular methyl, ethyl, n-propyl, isopropyl, n-butyl or isobutyl, wherein $R^1$–$R^7$ may be identical or different, and $R^8$ represents a linear or branched $C_1$–$C_6$-alkyl group, in particular methyl, ethyl, n-propyl, isopropyl, n-butyl or isobutyl.

The invention also provides a process for preparing compounds of the formula 1

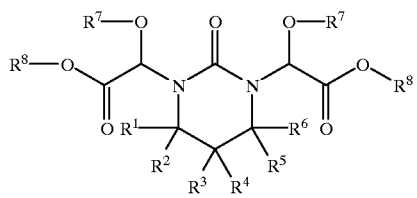

in which each of $R^1$–$R^7$ represents a hydrogen atom or a linear or branched $C_1$–$C_4$-alkyl group, in particular methyl, ethyl, n-propyl, isopropyl, n-butyl or isobutyl, wherein $R^1$–$R^7$ may be identical or different, and $R^8$ represents a linear or branched $C_1$–$C_6$-alkyl group, in particular methyl, ethyl, n-propyl, isopropyl, n-butyl or isobutyl, which is characterized in that a compound of the formula 2

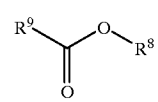

in which $R^9$ represents a member selected from the group comprising —CHO, —CH(OH)—$OR^8$ and —CH(OH)$_2$ and $R^8$ is defined as above, is reacted with a urea derivative of the formula 3,

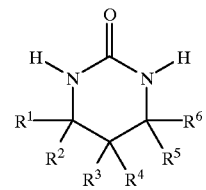

in which $R^1$–$R^6$ are defined as above, and the reaction product obtained is optionally reacted with an alcohol of the formula X—OH, in which X represents a linear or branched $C_1$–$C_4$-alkyl group.

The invention also provides the use of compounds of the formula 1,

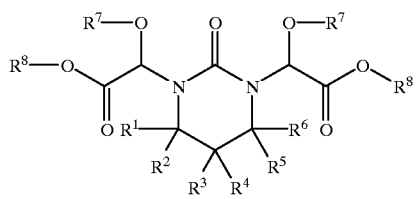

in which each of $R^1$–$R^7$ represent a hydrogen atom or a linear or branched $C_1$–$C_4$-alkyl group, preferably methyl, ethyl, n-propyl, isopropyl, n-butyl or isobutyl, wherein $R^1$–$R^7$ may be identical or different, and $R^8$ represents a linear or branched $C_1$–$C_6$-alkyl group, preferably methyl, ethyl, n-propyl, isopropyl, n-butyl or isobutyl, for hardening hydroxyl group-containing polymers.

As specified above, new compounds of the formula 1 according to the invention,

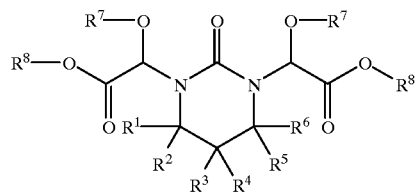

in which the substituents $R^1$–$R^7$ and $R^8$ are defined as above are provided. Examples of compounds in accordance with the present invention which are defined by the formula 1 given above, are as follows:

methyl hydroxy-[3-(hydroxy-methoxycarbonyl-methyl)-2-oxo-tetrahydro-pyrimidin-1-yl] acetate,
methyl hydroxy-[3-(hydroxy-ethoxycarbonyl-methyl)-2-oxo-tetrahydro-pyrimidin-1-yl] acetate,
butyl hydroxy-[3-(hydroxy-butoxycarbonyl-methyl)-2-oxo-tetrahydro-pyrimidin-1-yl] acetate,
methyl methoxy-[3-(methoxy-methoxycarbonyl-methyl)-2-oxo-tetrahydro-pyrimidin-1-yl] acetate,
ethyl ethoxy-[3-(ethoxy-ethoxycarbonyl-methyl)-2-oxo-tetrahydro-pyrimidin-1-yl] acetate,
butyl butoxy-[3-(butoxy-butoxycarbonyl-methyl)-2-oxo-tetrahydro-pyrimidin-1-yl] acetate,
methyl hydroxy-[3-(hydroxy-methoxycarbonyl-methyl)-5,5-dimethyl-2-oxo-tetrahydro-pyrimidin-1-yl] acetate and,
methyl hydroxy-[3-(hydroxy-methoxycarbonyl-methyl)-5,5-dimethyl-4-isopropyl-2-oxo-tetrahydro-pyrimidin-1-yl] acetate.

Preferred examples of compounds according to the invention having the formula 1 mentioned above are methyl hydroxy-[3-(hydroxy-methoxycarbonyl-methyl)-2-oxo-tetrahydro-pyrimidin-1-yl] acetate, ethyl hydroxy-[3-(hydroxy-ethyloxycarbonyl-methyl)-2-oxo-tetrahydro-pyrimidin-1-yl] acetate and butyl hydroxy-[3-(hydroxy-butoxycarbonyl-methyl)-2-oxo-tetrahydro-pyrimidin-1-yl] acetate.

The compounds according to the invention are prepared by first reacting a compound of the formula 2

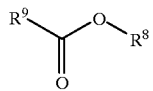

in which $R^9$ and $R^8$ are defined as above, with a urea derivative of the formula 3

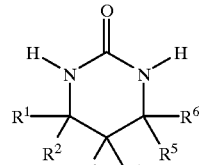

in which $R^1$–$R^6$ are defined as above.

Preferred examples of starting compounds of the formula 2 are:

methyl glyoxylate,
methyl glyoxylate hydrate,
ethyl glyoxylate,
propyl glyoxylate,
butyl glyoxylate,
methyl glyoxylate methyl-hemiacetal,
ethyl glyoxylate ethyl-hemiacetal,
propyl glyoxylate propyl-hemiacetal,
butyl glyoxylate butyl-hemiacetal.

Some of the glyoxylates and glyoxylate alkyl-hemiacetals can be obtained commercially or they may be prepared using known methods in organic chemistry such as, e.g., by esterification of glyoxylic acid with alcohols or by ozonolysis of dialkyl maleates. Hydrates such as, e.g., methyl glyoxylate hydrate and butyl glyoxylate hydrate may be prepared from methyl or butyl tartrate by oxidative C—C cleavage using periodic acid (L. D. M. Lolkema et al., Tetrahedron 50 (24) (1994) 7115–7128).

Compounds of the formula 3 are obtainable commercially such as, e.g., propylene urea. Otherwise they may be prepared using known methods in organic chemistry such as, e.g., by reacting amines with carbon dioxide or phosgene (C. Ferri, "Reaktionen der Organischen Chemie", Georg Thieme Verlag Stuttgart, 1978, page 657). Examples of these types of substituted propylene ureas are:

5-methyl-2-oxo-tetrahydro-pyrimidine,
5,5-dimethyl-2-oxo-tetrahydro-pyrimidine and
5,5-dimethyl-4-isopropyl-2-oxo-tetrahydro-pyrimidine (see GB patent 1 173 432).

The reaction of propylene ureas of the formula 3 with derivatives of the formula 2 can be performed in the temperature range from room temperature to elevated temperatures. In general a temperature range of 25–100° C. is expedient. Reaction temperatures in the range of 25–70° C. are preferred, in particular 50–70° C. In the temperature range of 70–100° C. no noticeable production of secondary products is observed. Reaction above 70° C., however, provides no further advantages with respect to yield or purity of the compounds.

Catalysts which are used according to the prior art for catalyzing reactions between ureas and carbonyl compounds, such as, e.g., inorganic bases such as sodium carbonate or sodium hydroxide are not required. The reaction may generally be performed without a solvent since compounds of the formula 2 are liquid. If a solvent is used, then any organic solvent which is inert towards aldehydes and ureas under the reaction conditions mentioned above are suitable; ethyl acetate or methylethyl ketone or toluene are preferred. The reaction is performed stoichiometrically, or preferably with a small excess of the more easily separated component. A molar ratio of 2.01–2.40 to 1, with respect to the component of the formula 2 to the component of the formula 3, is particularly advantageous. Reaction times are generally 1 to 5 hours.

In the following, the different reactions leading to compounds according to the invention, depending on the starting compound of the formula 2 which is used, are described in more detail.

1. When reacting a free aldehyde of the formula 2 ($R^9$=—CHO) with a urea derivative of the formula 3 no cleavage products are formed.

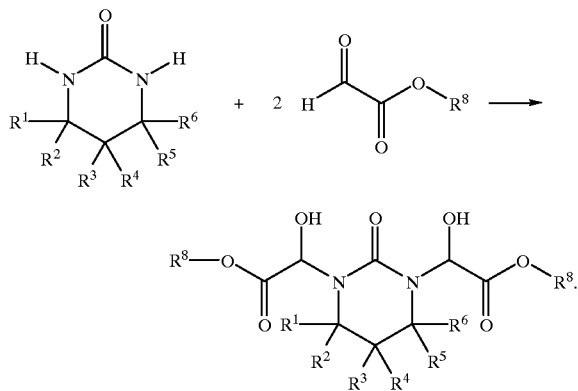

2. When reacting a glyoxylate alkyl-hemiacetal of the formula 2 ($R^9$=—CH(OH)—$OR^8$) with a urea derivative of the formula 3, cleavage products, such as, e.g., alcohols, are produced which can be removed under reduced pressure.

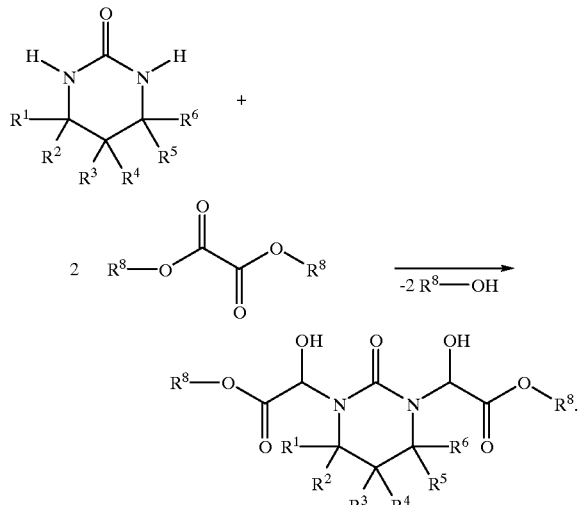

3. When reacting a stable hydrate of a glyoxylic acid derivative of the formula 2 ($R^9$=—CH(OH)$_2$) with a urea derivative of the formula 3, water is produced as a cleavage product which may be removed under reduced pressure.

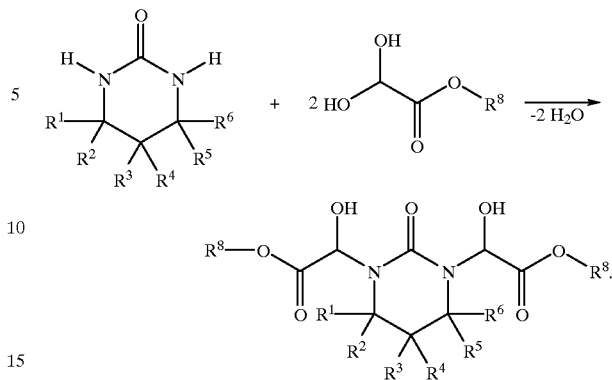

The reaction products obtained are usually isolated by precipitating in a solvent. Solvents for this purpose which readily dissolve compounds of the formula 2 are used in order to separate the excess of glyoxylic acid derivative.

Suitable solvents are, e.g., ketones, esters, aromatic hydrocarbons, preferably acetone, ethyl acetate or toluene. The products obtained are colorless and generally crystalline, water soluble and monomeric. The purity is more than 90%, often more than 95%. Products with longer alkyl chains are produced as pale oils and are only slightly water-soluble. The product may be purified by removing excess reactants by distillation under reduced pressure.

If the compounds according to the invention for use in mixtures are intended to be soluble in non-polar organic solvents, the reaction products obtained in the first stage may be etherified with an alcohol (X—OH, wherein X represents a linear or branched $C_{1-4}$-alkyl group, in particular methyl, ethyl, n-propyl, isopropyl, n-butyl or isobutyl). This leads to products of the formula 1 in which $R^7$ represents a linear or branched $C_1$–$C_4$-alkyl group, in particular methyl, ethyl, n-propyl, isopropyl, n-butyl or isobutyl and $R^1$–$R^6$ and $R^8$ are defined as above.

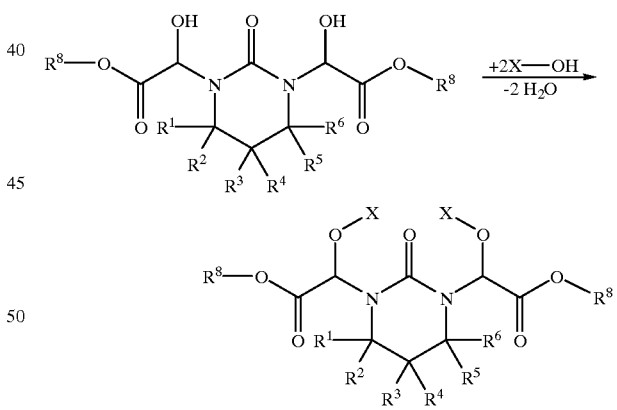

For etherification, the reaction products obtained which contain free hydroxyl groups are reacted with a 2 to 10-fold excess of alcohol, preferably 2 to 5-fold, in the presence of an acid catalyst. Methanol, ethanol, propanol, isopropanol, n-butanol and isobutanol are preferably used as alcohols. Medium to strong acids may be used as catalysts, preferably sulfuric acid, phosphoric acid, methanesulfonic acid, chlorosulfonic acid, benzenesulfonic acid, p-toluenesulfonic acid, naphtholsulfonic acid, chloroacetic acid or oxalic acid. The water produced during reaction is distilled off together with excess alcohol. If the alcohol used is not miscible with water, such as, e.g., n-butanol, it is distilled off azeotropically.

The compounds of the formula 1 according to the invention produced from propylene ureas and glyoxylate derivatives are colorless and thus advantageously differ from some of the reaction products described in U.S. Pat. No. 4,770,668 produced from ethylene ureas and glyoxylate derivatives, which are often dark colored. Analytical methods such as, e.g., gel permeation chromatography show that the compounds according to the invention contain no oligomeric fractions and are thus highly suitable for hardening polymers which contain hydroxyl groups.

Examples of hydroxyl group-containing polymers are hydroxyl group-containing polyacrylates and polyester polyols. The preparation of these types of polymers is known and is part of the general prior art. The polymers may be present as emulsions, dispersions, as solutions in water or organic solvents or as solids. Hardening the polymers with the compounds according to the invention of the formula 1 may be performed by reacting the compounds according to the invention with the polymers in any of the forms mentioned above, in the temperature range of 25–180° C., preferably 100–150° C. This cross-linking reaction may also be performed in the presence of an acid catalyst which accelerates the reaction. Organic acids or Lewis acids such as benzenesulfonic acid, p-toluenesulfonic acid, naphthalenesulfonic acid, oxalic acid, chloroacetic acid, methanesulfonic acid, citric acid, magnesium chloride, ammonium tetrafluoroborate and 2-hydroxyethylamino hydrochloride are suitable for this purpose.

The invention is explained by the following examples to which the invention is not limited.

EXAMPLE 1

Preparation of methyl hydroxy-[3-(hydroxy-methoxycarbonyl-methyl)-2-oxo-tetrahydro-pyrimidin-1-yl] acetate

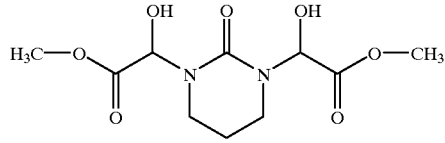

100.0 g (1.0 mol) of propylene urea were mixed with 245.0 g (2.04 mol) of methyl glyoxylate methyl-hemiacetal (manufacturer DSM Chemie Linz). The mixture was then stirred for 4 hours at 60° C. 500 ml of acetone were then added to the mixture, it was stirred and the precipitate was filtered off and dried.

Yield: 193.3 g

Melting point: 129° C.

$^1$H-NMR (300 MHz, $D_2O$): δ=5.61 (s, 2H), 4.65 (s, 6H), 3.65 (s, 6H), 3.40 (m, 2H), 3.25 (m, 2H), 1.95 (m, 2H).

$^{13}$C-NMR (300 MHz, $D_2O$): δ=172.3 (C=O), 157.5 (C=O), 79.2 (C—H), 54.4 (O—$CH_3$), 42.2, 20.5.

EXAMPLE 2

Preparation of ethyl hydroxy-[3-(hydroxy-ethoxycarbonyl-methyl)-2-oxo-tetrahydro-pyrimidin-1-yl] acetate

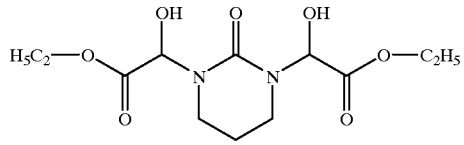

100.0 g (1.0 mol) of propylene urea were mixed with 408.0 g (2.00 mol) of ethyl glyoxylate (50% solution in toluene, manufacturer Fluka). This was stirred for 4 hours at 65° C. The solvent toluene was then removed under reduced pressure. The product was then obtained as a colorless residue.

Yield: 501 g $^1$H-NMR (300 MHz, $d^6$-acetone): δ=5.54 (d, 2H), 4.23 (m, 4H), 3.45 (m, 2H), 3.30 (q, 4H), 1.05 (t, 6H).

$^{13}$C-NMR (300 MHz, $d^6$-acetone): δ=171.5 (C=O), 156.1 (C=O), 79.8 (C—H), 66.4 (O—$CH_2$), 42.4, 20.6, 15.8 ($CH_3$).

EXAMPLE 3

Preparation of butyl [3-(hydroxy-butoxycarbonyl-methyl)-2-oxo-tetrahydro-pyrimidin-1-yl] acetate

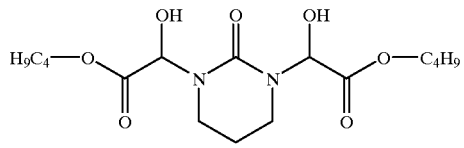

16.0 g (0.16 mol) of propylene urea were mixed with 49.4 g (0.38 mol) of butyl glyoxylate (manufacturer: Hoechst France). This mixture was stirred for 3 hours at 60° C., wherein the urea went into solution. A pale colored oil was produced. Then the excess of butyl glyoxylate was removed under vacuum (p=0.1 mbar) at 50° C.

Yield: 58.3 g $^1$H-NMR (300 MHz, $d^6$-acetone): δ=5.51 (d, 2H), 4.20 (m, 4H), 3.45 (m, 2H), 3.30 (m, 2H), 1.97 (m, 2H), 1.65 (m, 4H), 1.45 (m, 4H), 0.95 (t, 6H).

$^{13}$C-NMR (300 MHz, $d^6$-acetone): δ=171.3 (C=O), 156.2 (C=O), 79.5 (C—H), 66.0 (O—$CH_2$), 42.4, 31.0, 23.5, 19.9, 13.8 ($CH_3$).

EXAMPLE 4

Etherification of the Hydroxyl Groups in the Products Obtained in Example 1 with N-butanol 82.5 g (0.29 mol) of the product from Example 1 were mixed with 214.6 g (2.40 mol) of n-butanol and then 1.0 g of p-toluenesulfonic acid was added. Water which was produced during reaction was removed by azeotropic distillation. After removal of the water had terminated, the mixture was neutralized with caustic soda solution and the excess n-butanol removed by distillation. The product was obtained as a colorless, viscous residue which was readily soluble in cyclohexane. Gas chromatographic analysis showed complete etherification of the hydroxyl groups.

Yield: 114 g

EXAMPLE 5

Preparation of methyl hydroxy-[3-(hydroxy-methoxycarbonyl-methyl)-5,5-dimethyl-2-oxo-tetrahydro-pyrimidin-1-yl] acetate

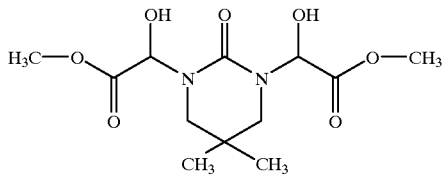

128.0 g (1.0 mol) of 5,5-dimethyl-2-oxo-tetrahydro-pyrimidine (prepared from 1,3-diamino-2,2-dimethyl-propane and urea) were mixed with 245.0 g (2.04 mol) of methyl glyoxylate methyl-hemiacetal (manufacturer DSM Chemie Linz). This was stirred for 4 hours at 70° C. 500 ml of acetone were added, the mixture was stirred and the precipitate filtered and dried.

Yield: 206 g

Melting point: 110–114° C.

$^{13}$C-NMR (300 MHz, d$^6$-DMSO): δ=173.3 (C=O), 155.5 (C=O), 79.2 (C—H), 55.5 (O—CH$_3$), 41.2, 31.5, 26.8.

EXAMPLE 6

Cross-linking with Hydroxyl Group-containing Polymers 13.0 g of the product from Example 4 and 0.7 g of p-toluenesulfonic acid were added to 100 g of a 60% resin solution consisting of a hydroxyl group-containing polyacrylate (having the composition: methyl methacrylate/ ethylhexyl acrylate/hydroxyethyl acrylate=50/25/25) and methylethyl ketone as solvent. A 50 μm thick layer of cross-linking mixture was applied to a steel sheet and cured for 20 minutes at a temperature of 140° C. The hardened film had a gel fraction of 96% and a very good solvent resistance towards methylethyl ketone and xylene.

Other embodiments of the present invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A process for preparing compounds of the formula 1

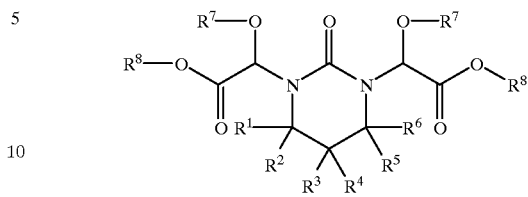

in which each of R$^1$–R$^7$ represents a hydrogen atom or a linear or a branched C$_1$–C$_4$-alkyl group, wherein R$^1$–R$^7$ may be identical or different, and R$^8$ represents a linear or branched C$_1$–C$_6$-alkyl group, comprising reacting a compound of the formula 2

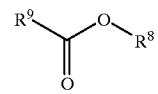

in which R$^9$ is selected from the group consisting of —CHO, —CH(OH)—OR$^8$, and —CH(OH)$_2$ and R$^8$ is defined as above, with a urea derivative of the formula 3

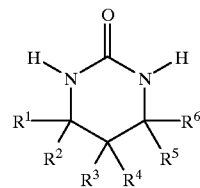

in which R$^1$–R$^6$ are defined as above, and the reaction product obtained is optionally reacted with an alcohol of the general formula X—OH, in which X represents a linear or branched C$_1$–C$_4$-alkyl group, wherein the compound of the formula 2 is reacted with the urea derivative of the formula 3 at a temperature of 25–100° C.

2. A process according to claim 1, wherein the linear or branched C$_1$–C$_4$ -alkyl group is a methyl, ethyl, n-propyl, isopropyl, n-butyl or isobutyl group.

3. A process according to claim 1, wherein the compound of the formula 2 is reacted with the urea derivative of the formula 3 at a temperature of 25–70° C.

4. A process according to claim 2, wherein the compound of the formula 2 is reacted with the urea derivative of the formula 3 at a temperature of 25–70° C.

5. A process according to claim 3, wherein the reaction is performed at a temperature in the range of 50–70° C.

6. A method according to claim 4, wherein the reaction is performed at a temperature in 50–70° C.

* * * * *